United States Patent
Wells

(10) Patent No.: US 12,029,260 B2
(45) Date of Patent: Jul. 9, 2024

(54) FLANGE OPENING FOR BRA

(71) Applicant: Sarah Wells, LLC, Fairfax, VA (US)

(72) Inventor: Sarah Wells, Fairfax, VA (US)

(73) Assignee: SARAH WELLS, LLC, Fairfax, VA (US)

( * ) Notice: Subject to any disclaimer, the term of this patent is extended or adjusted under 35 U.S.C. 154(b) by 77 days.

(21) Appl. No.: 17/880,112

(22) Filed: Aug. 3, 2022

(65) Prior Publication Data

US 2024/0041136 A1    Feb. 8, 2024

(51) Int. Cl.
*A41C 3/04* (2006.01)
*A61M 1/06* (2006.01)

(52) U.S. Cl.
CPC .............. *A41C 3/04* (2013.01); *A61M 1/062* (2014.02)

(58) Field of Classification Search
CPC ..................................................... A61M 1/062
See application file for complete search history.

(56) References Cited

U.S. PATENT DOCUMENTS

| | | | | |
|---|---|---|---|---|
| 4,289,137 A * | 9/1981 | Dell | ............ | A41C 3/02 2/912 |
| 4,633,876 A * | 1/1987 | Scullin | ............ | A41C 3/04 450/36 |
| 5,873,768 A * | 2/1999 | Fleischman-Ament | ............ | A41C 3/0071 450/67 |
| 5,944,579 A * | 8/1999 | Fleischman | ............ | D04B 1/24 2/73 |
| 6,550,067 B2 * | 4/2003 | Force | ............ | A41D 1/215 2/104 |
| 6,839,908 B2 * | 1/2005 | Schneider | ............ | A41D 1/215 2/104 |
| 6,855,029 B2 * | 2/2005 | Rothman | ............ | A41D 1/215 2/104 |
| 8,137,153 B2 * | 3/2012 | Bell | ............ | A61M 1/067 604/74 |
| 8,206,196 B1 * | 6/2012 | Martins-Crawbuck | ............ | A41C 3/0007 450/41 |
| 8,267,740 B1 * | 9/2012 | Afxentiou | ............ | A41C 3/0021 450/86 |
| 8,932,104 B2 * | 1/2015 | Moylan | ............ | A41C 3/0057 450/23 |
| 11,717,036 B2 * | 8/2023 | Carlino | ............ | A41D 1/215 450/36 |
| 2001/0039672 A1 * | 11/2001 | Force | ............ | A41D 1/215 2/104 |
| 2010/0185144 A1 * | 7/2010 | Bell | ............ | A61M 1/062 604/74 |

(Continued)

*Primary Examiner* — Jocelyn Bravo
(74) *Attorney, Agent, or Firm* — POLSINELLI PC

(57) ABSTRACT

Disclosed is a breast pump support garment. The garment secures a breast pump intake component to the breasts of a user with horizontal openings created by panels that are secured at one or both ends by bar tacks. The bar tacks resist further expansion of the opening by providing better structural support at its ends. An upper support is also provided with bar tacks extending vertically upward to provide better support and geometric positioning of the opening. An elastic band or ribbon can be sandwiched between two fabric panels around the periphery of the garment, and the panels of the garment can be a combination of single and multiple ply to provide more rigid and flexible portions.

6 Claims, 6 Drawing Sheets

(56) References Cited

U.S. PATENT DOCUMENTS

| | | | |
|---|---|---|---|
| 2011/0314587 A1* | 12/2011 | Ritchie | A41C 3/04 2/104 |
| 2012/0302137 A1* | 11/2012 | Moylan | A41C 3/0057 450/86 |
| 2013/0005217 A1* | 1/2013 | Afxentiou | A41C 3/0028 450/86 |
| 2018/0103691 A1* | 4/2018 | Alva | A41C 3/04 |
| 2020/0046036 A1* | 2/2020 | Guzman | A41C 3/12 |
| 2020/0297042 A1* | 9/2020 | Carlino | A41D 1/215 |
| 2023/0320435 A1* | 10/2023 | Carlino | A41C 3/08 450/36 |

* cited by examiner

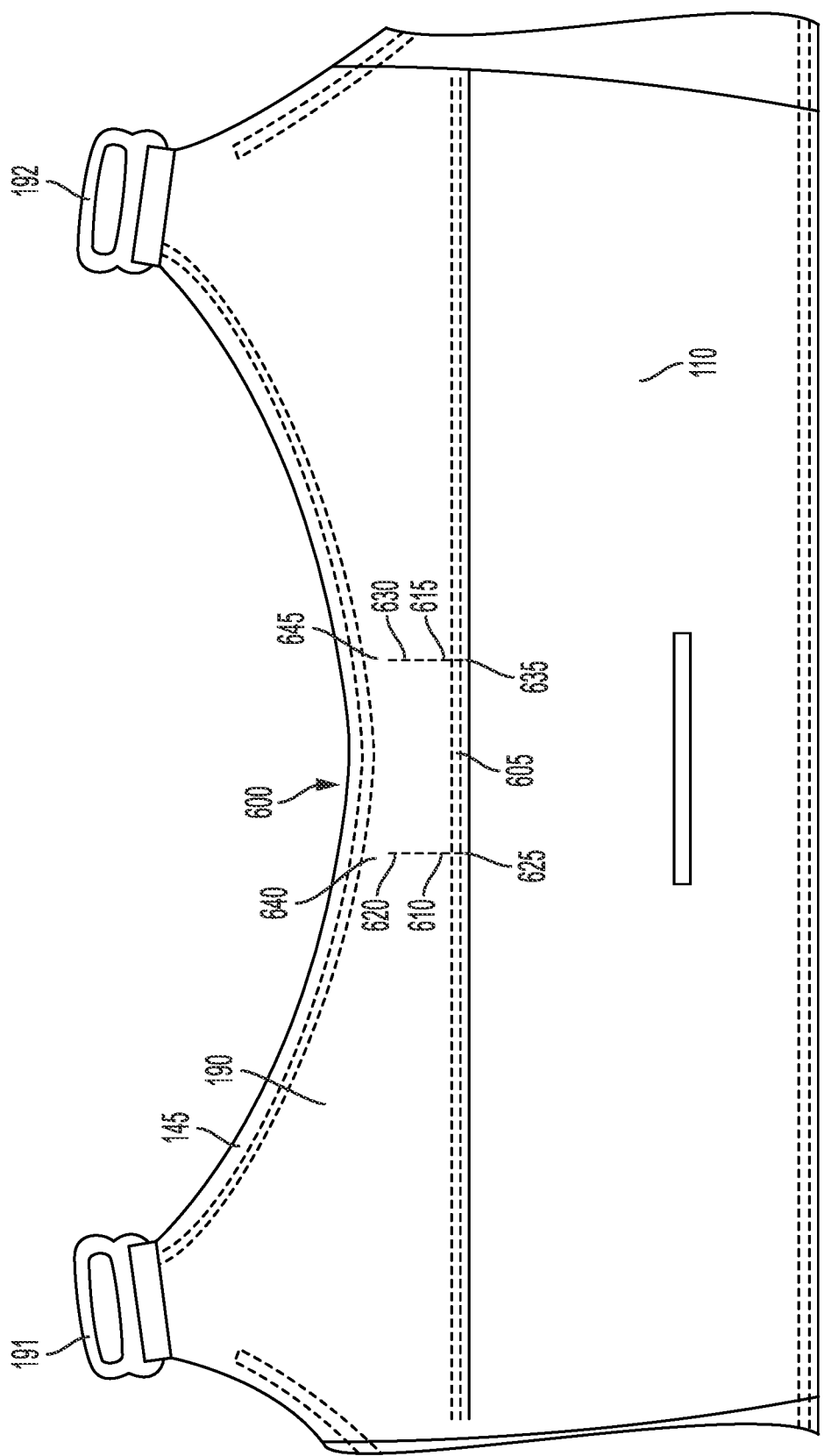

FLANGE OPENING FOR BRA

TECHNICAL FIELD OF THE INVENTION

The presently disclosed embodiments relate generally to nursing bras. More particularly, the presently disclosed embodiments relate to nursing bras with a flange opening permitting easier insertion and removal of breast pump intake components.

BACKGROUND OF THE INVENTION

Breast pumps are ubiquitous across western society. A new mother can use a breast pump to extract natural milk for their baby and to thereafter store the milk for later usage. Mothers also pump to alleviate build up within their breasts, and for a myriad of other reasons.

Many mothers pump milk in areas where other people are present. Women pump in the workplace or in public, and naturally prefer to conceal their breasts during the process of pumping. Prior art nursing bras were created to permit mothers to pump in the presence of others while still concealing their breasts and maintaining the breast pump in place.

One such example of a pump is described in U.S. Pat. No. 8,137,153. This prior art patent describes a nursing bra with openings to accommodate breast pump intake components and maintain the intake components in place. However, the openings are structured by a simple lack of stitching in a "stitched-unstitched-stitched" configuration. This arrangement can be weak and lead to tearing of the opening without other structural elements to maintain the opening in place.

Another prior art nursing bra is described in U.S. Patent Application Publication No. 2017/0042256. Here, however, the opening is a simple hole and is too small to accommodate larger breast pump intake components.

Yet another nursing bra is described in U.S. Pat. No. 8,469,770. This nursing bra includes a low horizontal opening in the front to receive an intake component from a breast pump. However, the rear panels of the bra are shaped differently with a multi-directional configuration so as to more securely restrict the breast pump intake component. In this instance, removability of the breast pump intake component may be difficult due to the multi-directional configuration in the rear of the bra.

SUMMARY OF THE INVENTION

The presently disclosed embodiments relate generally to a breast pump support garment that secures a breast pump intake component to the breasts of a user while permitting easy removal and insertion of the intake component. The garment includes openings and panels that cooperatively secure the breast pump intake component to the user's breasts through horizontal openings that permit insertion of a variety of different size intake components. The openings are secured at one or both ends by bar tacks that resist further expansion of the opening and provide better structural support at its ends. An upper support also includes bar tacks that extend vertically upward either intermittently or continuously to provide better support and geometric positioning of the opening for insertion and removal of the intake component. Some embodiments can also include elastic sandwiched between two fabric panels and extending around the periphery of the garment. Some embodiments can include an outer panel that is made of a single panel to permit flexibility, with an inner panel and upper flap that are made of a multiple fabric configuration.

In particular, the presently disclosed embodiments include a garment that includes an outer panel and an inner panel. The inner panel overlaps with the outer panel and couples to the outer panel at a main seam such that the outer panel and inner panel define a first opening at a first side of the main seam and a second opening at a second side of the main seam. The garment further includes a first wing coupled to a first side of one at least one of the outer panel and inner panel and a second wing coupled to a second side of at least one of the outer panel and inner panel. The second side of the outer panel and/or the inner panel is opposite the first side of the outer panel and/or the inner panel. First and second bar tacks can be respectively located at first and second opposite ends of the main seam. Further, first and second shoulder straps can be coupled to at least one of the outer panel and inner panel at a first end of the shoulder straps and coupled to the first wing and the second wing, respectively, at a second end of the shoulder straps.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

FIG. 6 is a partial enlarged view of the breast pump support garment illustrating an upper support according to at least some of the presently disclosed embodiments.

DETAILED DESCRIPTION OF THE EMBODIMENTS

Figure 1:
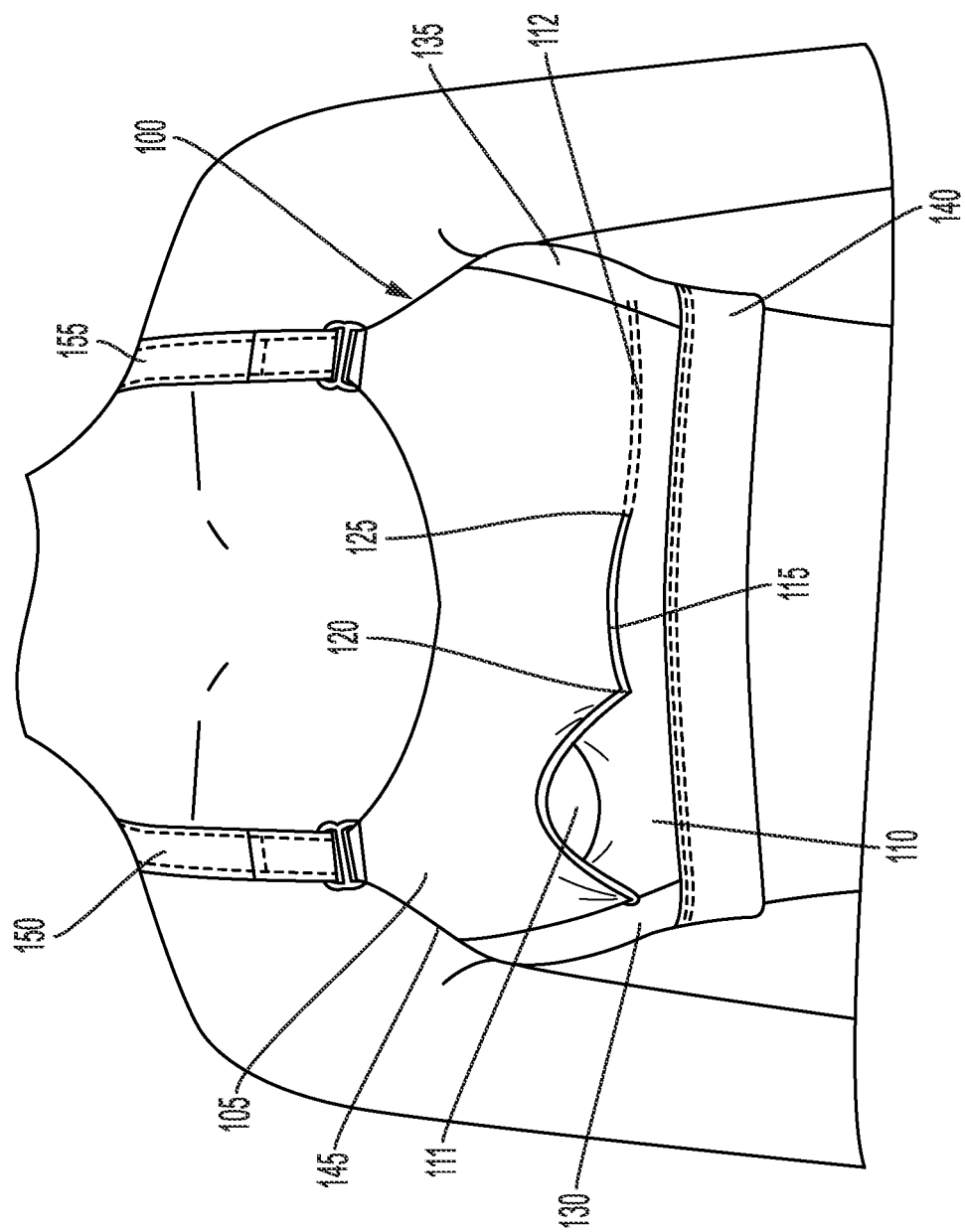
FIG. 1 is a front view of a breast pump support garment positioned on a user with one of the openings in the open position, according to at least some of the presently disclosed embodiments.
Figure 2:
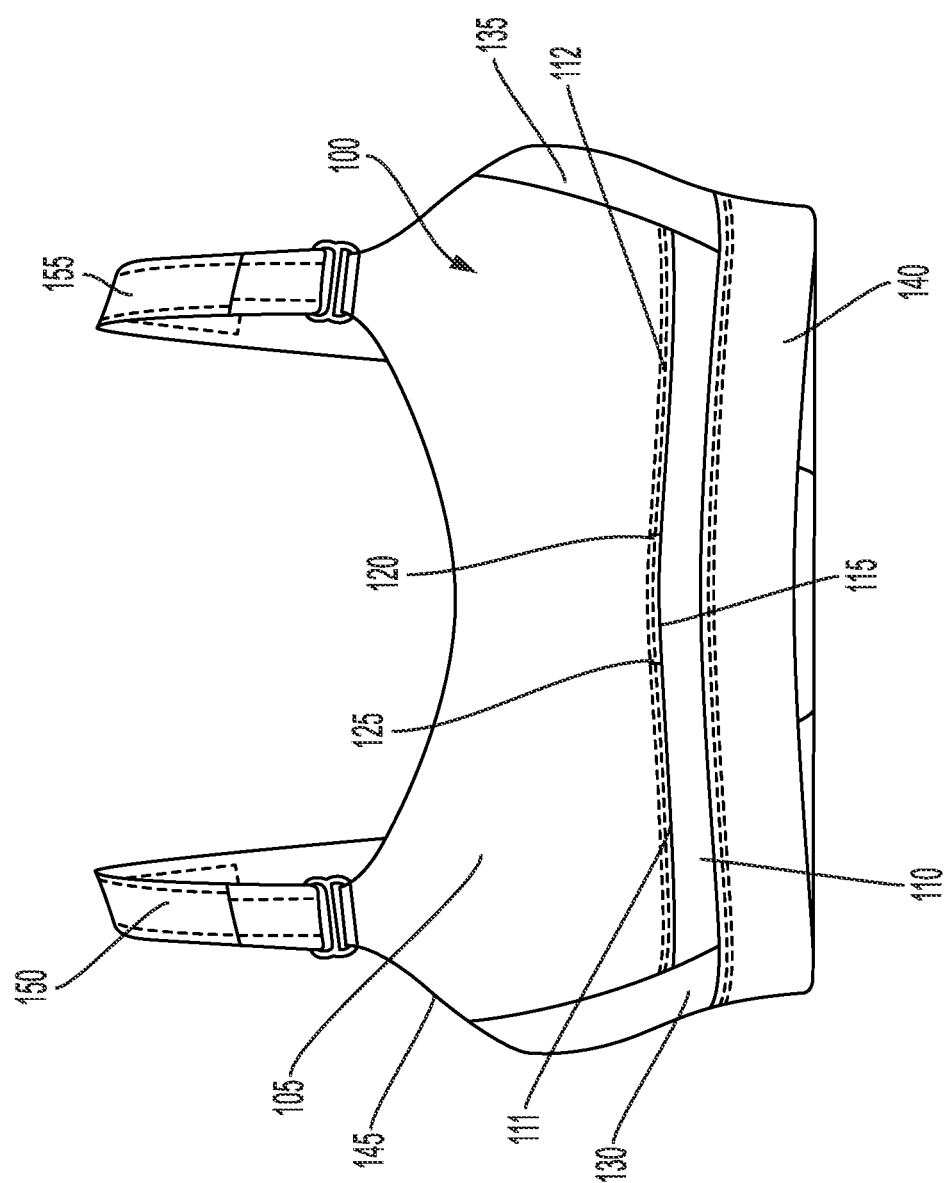
FIG. 2 is a front view of a breast pump support garment positioned without a user and with both of the openings in the closed position, according to at least some of the presently disclosed embodiments.

While this invention is susceptible of embodiments in many different forms, there is shown in the drawings, and will herein be described in detail, a preferred embodiment of the invention with the understanding that the present disclosure is to be considered as an exemplification of the principles of the invention and is not intended to limit the broad aspect of the invention to embodiments illustrated. As used herein, the term "present invention" is not intended to limit the scope of the claimed invention and is instead a term used to discuss exemplary embodiments of the invention for explanatory purposes only.

The presently disclosed embodiments relate generally to a breast pump support garment. The garment secures a breast pump intake component to the breasts of a user with openings and panels. The openings are horizontal openings that allow for the insertion of a variety of different size intake components and that are secured at one or both ends by bar tacks that resist further expansion of the opening and provide better structural support at its ends. The support garment can also include an upper support that has bar tacks extending vertically upward to provide better support and geometric positioning of the opening. Some embodiments can also include an elastic band or ribbon that is sandwiched between two fabric panels around the periphery of the garment; or a combination of single and multiple ply portions of the panels to provide more rigid and flexible portions.

As shown in FIGS. 1-5, the presently disclosed embodiments can include a breast pump support garment 100 with an outer panel 105 and an inner panel 110 coupled to one another so as to form a first opening 111 and a second opening 112. The first opening 111 and second opening 112 can be separated by a main seam 115 that can be positioned in a middle of the garment 100 and couple the outer panel 105 to the inner panel 110. The main seam 115 can include a first main seam bar tack 120 and a second main seam bar tack 125 at the extreme horizontal ends of the main seam 115. In doing so, the main seam 115 can be secured at its outer ends and resist ripping or unthreading due to the repeated opening and closing of the openings 111, 112. In some embodiments, the main seam 115 can be shorter than either opening 111, 112 to permit a wide variety of breast pump intake components to be inserted into the openings 111, 112. In some embodiments, and as shown the outer panel 105 can overlap the inner panel 110 to provide better concealment of the user's breasts.

The garment 100 can include a first side panel 130 and a second side panel 135 that couple to the outer panel 105 and inner panel 110 at their horizontal edges. The garment 100 can also include an elastic band 140 located at a lower portion of the garment 100 to secure the garment 100 around the torso of the user. A perimeter 145 of the garment 100 can include an elastic band or ribbon that is sandwiched between two or more pieces of fabric to be concealed while still providing an elastic effect around the perimeter 145 of the garment 100. For example, the elastic band or ribbon can be in between two pieces of fabric for a single panel (if the panel is multi-ply) or between two or more panels (if at least one of the sandwiching panels is single ply). In combination with the elastic band 140, the elastic around the periphery 145 can secure the garment 100 to the user in a comfortable but structurally stable manner. Similarly, the outer panel 105 can include an elastic member sandwiched by or otherwise secured to the outer panel at the first opening 111 and the second opening 112, as shown in, for example, FIG. 1. The elastic member can provide elastic bias so as to better maintain a breast pump intake component during use.

The garment 100 can include additional elements commonly found in conventional bras. For example, the garment 100 can include a first shoulder strap 150 and a second shoulder strap 155. As shown in FIGS. 1-5, the first shoulder strap 150 and second shoulder strap 155 can be coupled to the outer panel 105 at the front of the garment 100, and can be coupled to a first wing 160 and a second wing 165, respectively, at the rear of the garment 100. In some embodiments, the first wing 160 and second wing 165 can be coupled directly to the outer panel 105 or inner panel 110 without the side panels 130, 135 therebetween. The shoulder straps 150, 155 can include any fastening structure, but in a preferred embodiment, include a "hook and loop" structure, also referred to as Velcro®. For example, the first shoulder strap 150 can include a first hook 170 that couples to a first loop 175, and the second shoulder strap 155 can include a second hook 180 that couples to a second loop 185.

Figure 3:
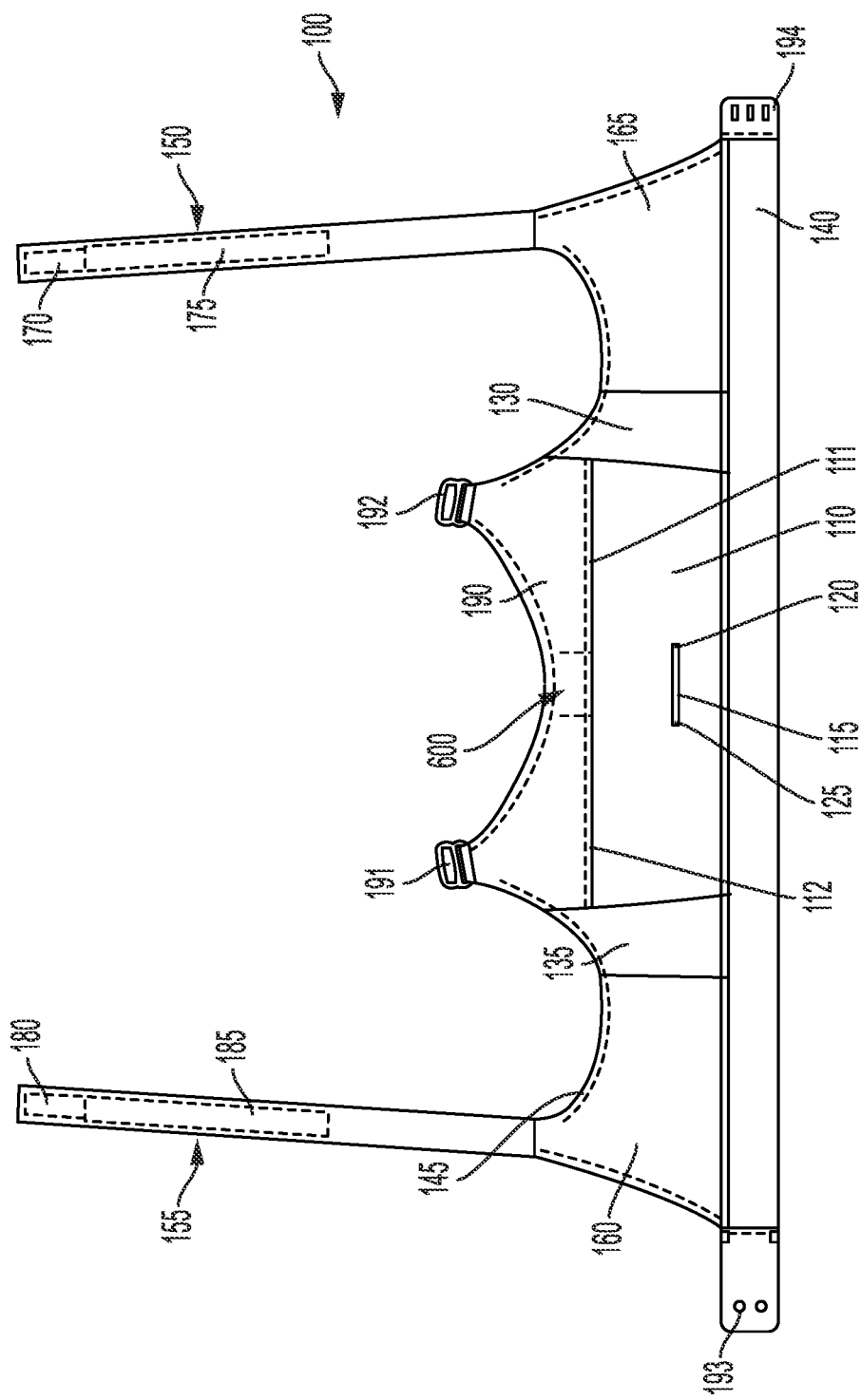
FIG. 3 is a rear view of a breast pump support garment extended flat in a horizontal position according to at least some of the presently disclosed embodiments.
Figure 4:
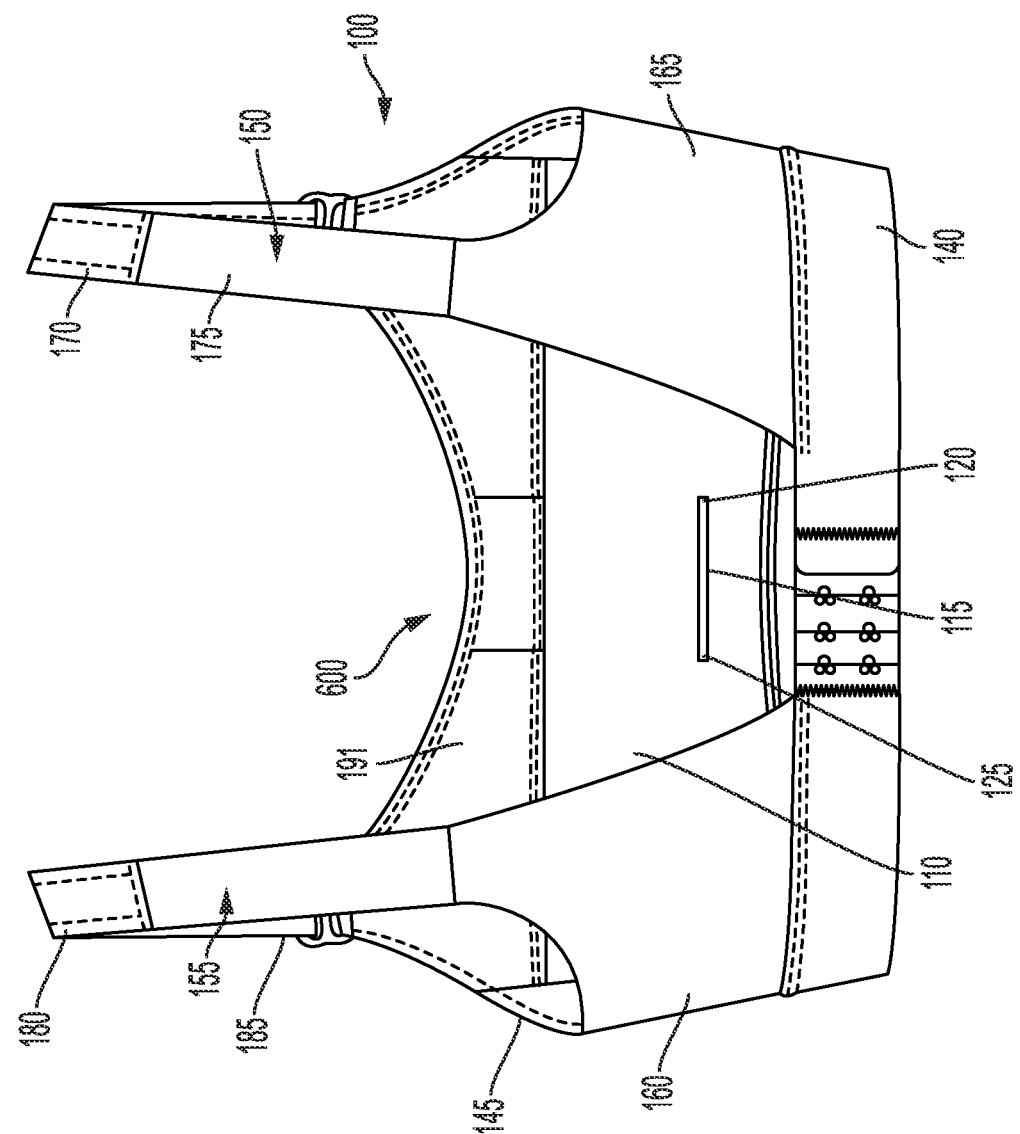
FIG. 4 is a rear view of a breast pump support garment positioned without a user according to at least some of the presently disclosed embodiments.
Figure 5:
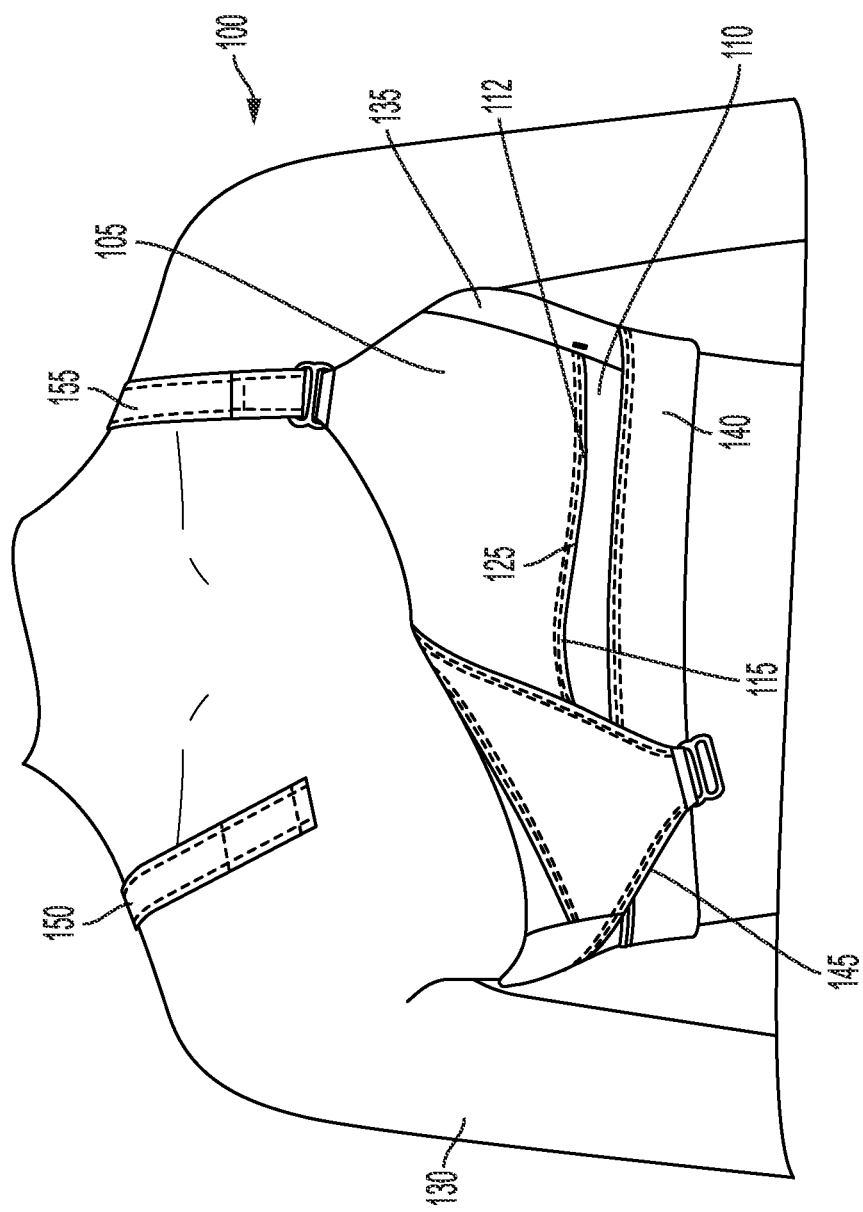
FIG. 5 is a front view of a breast pump support garment positioned on a user with one of the shoulder straps in the disconnected position, according to at least some of the presently disclosed embodiments.

The garment 100 can include an upper flap 190 with a first slot 191 and a second slot 192 extending therefrom. The slots 191, 192 can allow for insertion of the shoulder straps 150, 155 and can couple to both the upper flap 190 and the outer panel 105 at the front of the garment 100. The shoulder straps 155, 160 can then couple to their respective wings 160, 165 (as shown in FIG. 3) at the rear of the garment 100, when the garment 100 is in a wearing position on a user. The shoulder straps 155, 160 can then insert through the slots 192, 191 and fold back over onto themselves to secure the hook and loop structure together, as best shown in FIG. 5. To secure the garment 100 horizontally, the user may couple a clasp 193 to an eye 194 in a conventional manner known in the brassiere field.

The various panels of the garment 100 can be either single-ply or multi-ply, or a combination of the two. For example, the garment 100 may include an outer panel 105 with a single-ply fabric panel to permit greater flexibility, while also including an inner panel 110 that is made of a multi-ply fabric panel. In doing so, the singly-ply outer panel 105 can be more flexible than the multi-ply inner panel to permit greater flexibility of the single-ply panel and permit easier insertion and removal of a breast pump intake component. The garment 100 can also include a single-ply inner panel 110 and multi-ply outer panel 105 for the same reasons. Any combination of single or multi ply panels can be implemented without departing from the spirit and scope of the present invention.

FIG. 6 is a partial enlarged view of the breast pump support garment 100 illustrating an upper support 600 according to at least some of the presently disclosed embodiments. As shown, the upper support 600 includes a horizontal seam 605, first vertical seam 610, and second vertical seam 615, that collectively couple the upper flap 190 to the inner panel 110. The first vertical seam 610 can be spaced horizontally from and parallel to the second vertical seam 615 to provide greater horizontal support. The structure of the upper support 600 is important in maintaining structural integrity of the garment 100 as a whole. It is also important for maintaining the geometry of the openings 111, 112 and permitting easier insertion and removal of the breast pump intake components. The vertical seams 610, 615 can be a continuous bar tack, or can include intermittent bar tacks to provide additional structural support to the garment 100. For example, the upper support 600 can include a first bar tack 620, a second bar tack 625, a third bar tack 630, and a fourth bar tack 635, located at the upper left, lower left, upper right, and lower right corners of the upper support 600, respectively. These bar tacks 620, 625, 630, 635 collectively define a first gap 640 between the first bar tack 620 and the perimeter 145, and a second gap 645 between the third bar tack 630 and the perimeter 145. These gaps 640, 645 permit greater flexibility and breathability of the garment 600 and avoid extending the stresses received by the upper support 600 to the perimeter 145.

A method of using the garment 100 will now be described. The user can first put on the garment 100 by coupling the clasp 193 to the appropriate set of eyes 194, depending on the preferred fit of the user. The user can then adjust the shoulder straps 150, 155 by detaching the first hook 170 and second hook 180 from the first loop 175 and second loop 185, respectively, and reattaching these components in the preferred orientation based on user fit. Thereafter, the user can lift up the outer panel as shown in FIG. 1 to expose the opening and insert the intake component, attaching it to the user's breast. The user can then adjust the outer panel 105 and the inner panel 110 to conceal the intake component. The breast pump itself can now be activated to extract milk from the user. To remove the intake component, simply follow the above process in reverse.

As used herein, the term "coupled" and its functional equivalents are not intended to necessarily be limited to direct, mechanical coupling of two or more components. Instead, the term "coupled" and its functional equivalents are intended to mean any direct or indirect mechanical, electrical, or chemical connection between two or more objects, features, work pieces, and/or environmental matter. "Coupled" is also intended to mean, in some examples, one object being integral with another object.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of the inventors' contribution. The actual scope of the protection sought is intended to be defined in the following claims when viewed in their proper perspective based on the prior art.

What is claimed is:

1. A garment comprising:
   an inner panel;
   an outer panel overlapping the inner panel and coupled to the inner panel at a main seam such that the outer panel and inner panel define a first opening at a first side of the main seam and a second opening at a second side of the main seam;
   a first wing coupled to a first side of one at least one of the outer panel and inner panel;
   a second wing coupled to a second side of at least one of the outer panel and inner panel, the second side of the outer panel and/or the inner panel being opposite the first side of the outer panel and/or the inner panel;
   first and second bar tacks respectively located at first and second locations of the main seam;
   first and second shoulder straps coupled to at least one of the outer panel and inner panel at a first end of the shoulder straps and coupled to the first wing and the second wing, respectively, at a second end of the shoulder straps;
   an upper flap coupled to an inner portion of the inner panel; and
   an upper support coupling the upper flap to the inner panel, the upper support including a first vertical seam and a second vertical seam spaced from the first vertical seam.

2. The garment of claim 1, wherein the first vertical seam is spaced horizontally from and parallel to the second vertical seam.

3. The garment of claim 1, further comprising a horizontal seam coupling the first vertical seam to the second vertical seam.

4. The garment of claim 1, wherein the upper flap extends to a perimeter of the garment and wherein the first and second vertical seams are spaced from the perimeter so as to form first and second gaps, respectively.

5. The garment of claim 1, wherein the upper support comprises at least one bar tack.

6. The garment of claim 5, wherein the at least one bar tack includes a first bar tack at a first end of the first vertical seam, a second bar tack at a second end of the first vertical seam opposite the first end of the first vertical seam, a third bar tack at a first end of the second vertical seam, and a fourth bar tack at a second end of the second vertical seam opposite the first end of the second vertical seam.

* * * * *